United States Patent
Zink et al.

(10) Patent No.: US 9,568,466 B2
(45) Date of Patent: Feb. 14, 2017

(54) IN VITRO ASSAY FOR PREDICTING RENAL PROXIMAL TUBULAR CELL TOXICITY

(71) Applicant: AGENCY FOR SCIENCE, TECHNOLOGY AND RESEARCH, Singapore (SG)

(72) Inventors: Daniele Zink, Singapore (SG); Yao Li, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 14/416,016

(22) PCT Filed: Jul. 22, 2013

(86) PCT No.: PCT/IB2013/001589
§ 371 (c)(1),
(2) Date: Jan. 20, 2015

(87) PCT Pub. No.: WO2014/013329
PCT Pub. Date: Jan. 23, 2014

(65) Prior Publication Data
US 2015/0219625 A1 Aug. 6, 2015

Related U.S. Application Data

(60) Provisional application No. 61/674,024, filed on Jul. 20, 2012.

(51) Int. Cl.
*G01N 33/50* (2006.01)
(52) U.S. Cl.
CPC ...... *G01N 33/5014* (2013.01); *G01N 33/5026* (2013.01); *G01N 33/5044* (2013.01); *G01N 2333/47* (2013.01); *G01N 2333/4712* (2013.01); *G01N 2458/00* (2013.01)
(58) Field of Classification Search
CPC .................................................. G01N 33/5026
See application file for complete search history.

(56) References Cited

U.S. PATENT DOCUMENTS

| | | | |
|---|---|---|---|
| 2009/0220982 A1 | 9/2009 | Armstrong et al. | |
| 2011/0236874 A1 | 9/2011 | Zink et al. | |

FOREIGN PATENT DOCUMENTS

| | | | |
|---|---|---|---|
| CN | 1520462 A | 8/2004 | |
| WO | 00/46404 A1 | 10/2000 | |
| WO | WO 2010/064995 A1 | 6/2010 | |
| WO | 2014/013334 A1 | 1/2014 | |

OTHER PUBLICATIONS

Akcay, et al., "Mediators of inflammation in acute kidney injury," Mediators Inflamm. 2009, vol. 2009, Article ID 137072, 12 page.
Araki, et al., "Expression of IL-8 during reperfusion of renal allografts is dependent on ischemic time," Transplantation 2006, 81(5):783-8.
Astashkina, et al., "A 3-D organoid kidney culture model engineered for high-throughput nephrotoxicity assays," Biomaterials 2012, 33(18):4700-11.
Astashkina, et al., "Comparing predictive drug nephrotoxicity biomarkers in kidney 3-D primary organoid culture and immortalized cell lines," Biomaterials 2012, 33(18):4712-21.
Atcherson, et al., "Cytotoxic effects of FK506 on human renal proximal tubule cells in culture," In Vitro Cell Dev Biol Anim. 1994, 30A(9):562-7.
Bach, et al., "In vitro methods for nephrotoxicity screening and risk assessment," In In vitro methods in pharmaceutical research, Academic Press Ltd, San Diego, 1997, pp. 55-101.
Bacon, et al., "In vitro assessment of trospectomycin and gentamicin sulphate in the LLC-PK(1) cell line," Toxicol In Vitro 1991, 5(5-6):473-8.
Baer, et al., "Effects of mycophenolic acid on IL-6 expression of human renal proximal and distal tubular cells in vitro", Nephrol Dial Transplant. 2004, 19(1):47-52.
Beeson, et al., "A high throughput respirometric assay for mitochondrial biogenesis and toxicity," Anal Biochem. 2010, 404(1):78-81.
Bens, et al., "Cell models for studying renal physiology," Pflugers Arch. 2008, 457(1):1-15.
Bonventre, et al., "Next-generation biomarkers for detecting kidney toxicity," Nat Biotechnol. 2010, 28(5):436-40.
Choudhury, et al., "Drug-associated renal dysfunction and injury," Nat Clin Pract Nephrol. 2006, 2(2):80-91.
De Graauw, et al., "Proteomic analysis of alternative protein tyrosine phosphorylation in 1,2-dichlorovinyl-cysteine-induced cytotoxicity in primary cultured rat renal proximal tubular cells," J Pharmacol Exp Ther. 2007, 322(1):89-100.
Dieterle, et al., "Renal biomarker qualification submission: a dialog between the FDA-EMEA and Predictive Safety Testing Consortium," Nat Biotechnol. 2010, 28(5):455-62.
Dietrich, et al., "Species- and sex-specific renal cytotoxicity of ochratoxin A and B in vitro," Exp Toxicol Pathol. 2001, 53(2-3):215-25.
Duff, et al., "Transepithelial resistance and inulin permeability as endpoints in in vitro nephrotoxicity testing," Altern Lab Anim. 2002, 30 Suppl 2:53-9.

(Continued)

*Primary Examiner* — Bin Shen
(74) *Attorney, Agent, or Firm* — Blakely, Sokoloff, Taylor & Zafman LLP

(57) ABSTRACT

There is provided an in vitro assay for screening a test compound for toxicity in renal proximal tubular cells. The method comprises contacting a test compound with a test population of renal proximal tubular cells; and examining one or more cell morphology features, examining one or more cytoskeleton features, and/or determining cell numbers of the renal proximal tubular cells in the test population and comparing such cell morphology, arrangement of cytoskeletal components and/or cell count with the respective features of a control population. A change in one or more cell morphology features, a change in arrangement of one or more cytoskeleton features or a decrease in cell numbers of the test population relative to the control population is indicative that the test compound is toxic for renal proximal tubular cells.

19 Claims, 11 Drawing Sheets

(56) References Cited

OTHER PUBLICATIONS

Duncan-Achanzar et al., "Inorganic mercury chloride-induced apoptosis in the cultured porcine renal cell line LLC-Pk!", Pharmacol. Exp. Ther., 1996, 277(3):1726-32.

Fuente Mora, et al., "Differentiation of podocyte and proximal tubule-like cells from a mouse kidney-derived stem cell line," Stem Cells Dev. 2012, 21(2):296-307.

Gerritsma, et al., "Regulation and production of IL-8 by human proximal tubular epithelial cells in vitro," Clin Exp Immunol. 1996, 103(2):289-94.

Gerritsma, et al., "Production of inflammatory mediators and cytokine responsiveness of an SV40-transformed human proximal tubular epithelial cell line," Exp Nephrol. 1998, 6(3):208-16.

Grigoryev, et al., "The Local and Systemic Inflammatory Transcriptome after Acute Kidney Injury," J Am Soc Nephrol. 2008, 19(3):547-58.

Guo, et al., "How to prevent, recognize, and treat drug-induced nephrotoxicity," Cleve Clin J Med. 2002, 69(4):289-90, 293-4, 296-7 passim.

Healy, et al., "Apoptosis and necrosis: mechanisms of cell death induced by cyclosporine A in a renal proximal tubular cell line," Kidney Int. 1998, 54(6):1955-66.

Ichimura, et al., "Kidney injury molecule-1: a tissue and urinary biomarker for nephrotoxicant-induced renal injury," Am J Physiol Renal Physiol. 2004, 286(3):F552-63.

Izzedine, et al., "The nephrotoxic effects of HAART" Nat Rev Nephrol. 2009, 5(10):563-73.

Jeannette, et al., "Hepinstall's Pathology of the Kidney," 6th Edition (vol. 2): Ischemic and Toxic Acute Tubular Injury and OtherIschemic Renal Injury, 2007, Lippincott Williams & Wilkins, pp. 1139-1198.

Jenkinson, et al., "The limitations of renal epithelial cell line HK-2 as a model of drug transporter expression and function in the proximal tubule," Pflugers Arch. 2012, 464(6):601-11.

Jennings, et al., "Assessment of a new cell culture perfusion apparatus for in vitro chronictoxicity testing. Part 2: toxicological evaluation," ALTEX 2004, 21(2):61-6.

Kapitsinou, et al., "Acute renal failure in an AIDS patient on tenofovir: a case report," J Med Case Rep. 2008, 2:94.

Kawakami, et al., "Indoxyl sulfate inhibits proliferation of human proximal tubular cells via endoplasmic reticulum stress," Am J Physiol Renal Physiol. 2010, 299(3):F568-76.

Kermanizadeh, et al., "An In Vitro Assessment of Panel of Engineered Nanomaterials Using a Human Renal Cell Line: Cytotoxicity, Pro-Inflammatory Response, Oxidative Stress and Genotoxicity", BMC Nephrol., 2013, 14(96):1-12.

Levy, et al., "The effect of acute renal failure on mortality. A cohort analysis," JAMA 1996, 275(19):1489-94.

Li et al., "Use of cultured cells of kidney origin to assess specific cytotoxic effects of nephrotoxins," Toxicol In Vitro 2003, 17(1):107-13.

Li, et al., "Human primary renal cells as a model for toxicity assessment of chemo-therapeutic drugs," Toxicol In Vitro 2006, 20(5):669-76.

Li, et al., "Effects of quantum dots on different renal proximal tubule cell models and on gel-free renal tubules generated in vitro," Nanotoxicology 2012, 6(2):121-33.

Li, et al., "An in vitro method for the prediction of renal proximal tubular toxicity in humans," Toxicol Res. 2013, 2:352-65.

Liang, et al., "Effects of interleukin 18 on injury and activation of human proximal tubular epithelial cells," Nephrology (Carlton) 2007, 12(1):53-61.

Limonciel, et al., "Lactate is an ideal non-invasive marker for evaluating temporal alterations in cell stress and toxicity in repeat dose testing regimes," Toxicol In Vitro 2011, 25(8):1855-62.

Lin, et al., "Evaluation of Drugs With Specific Organ Toxicities in Organ-Specific Cell Lines," Toxicol Sci. 2012, 126 (1):114-27.

Luger, et al., "Evidence for an epidermal cytokine network," J Invest Dermatol. 1990, 95(6 Suppl):100S-104S.

McMorrow, et al., "Cyclosporine A induced epithelial-mesenchymal transition in human renal proximal tubular epithelial cells," Nephrol Dial Transplant 2005, 20(10):2215-25.

Miller, et al., "Tetracycline-induced renal failure after dental treatment," JADA 2009, 140(1):56-60.

Miller, et al., "Mechanisms of Cisplatin nephrotoxicity," Toxins (Basel) 2010, 2(11):2490-518.

Mishra, et al., "Identification of neutrophil gelatinase-associated lipocalin as a novel early urinary biomarker for ischemic renal injury," J Am Soc Nephrol. 2003, 14(10):2534-43.

Miyauchi, et al., "Upregulated IL-18 expression in type 2 diabetic subjects with nephropathy: TGF-beta1 enhanced IL-18 expression in human renal proximal tubular epithelial cells," Diabetes Res Clin Pract. 2009, 83(2):190-9.

Moffett, et al., "Acute Kidney Injury and Increasing Nephrotoxic-Medication Exposure in Noncritically-Ill Children," Clin J Am Soc Nephrol. 2011, 6(4):856-63.

Mora, et al., "Differentiation of podocyte and proximal tubule-like cells from a mouse kidney-derived stem cell line", Stem Cells Dev., 2011, 21(2):296-307.

Narayanan, et al., "Human embryonic stem cells differentiate into functional renal proximal tubular-like cells," Kidney Int. 2013, 83:593-603.

Nash, et al., "Hospital-acquired renal insufficiency," Am J Kidney Dis. 2002, 39(5):930-6.

Nechemia-Arbely et al., "Il-6/Il-6R Axis Plays a Critical Role in Acute Kidney Injury", J. Am. Soc. Nephrol., 2008, 19(6):1106-15.

Ni, et al., "Characterization of Membrane Materials and Membrane Coatings for Bioreactor Units of Bioartificial Kidneys," Biomaterials 2011, 32(6):1465-76.

Ni, et al., "The Use of a Library of Industrial Materials to Determine the Nature of Substrate-Dependent Performance of Primary Adherent Human Cells," Biomaterials 2012, 33(2):353-64 (E-pub 2011).

Niemir, et al., "The in situ expression of interleukin-8 in the normal human kidney and in different morphological forms of glomerulonephritis," Am J Kidney Dis. 2004, 43(6):983-98.

Perazella, "COX-2 inhibitors and the kidney," Hosp Pract (Minneap) 2001, 36(3):43-6, 55-6.

Pfaller, et al., "Nephrotoxicity testing in vitro—what we know and what we need to know," Environ Health Perspect. 1998, 106(Suppl 2):559-69.

Phillips, et al., "Tetracycline Poisoning in Renal Failure," Br Med J. 1974, 2(5911):149-51.

Predict-IV, 3rd Annual Periodic Report, Jun. 30, 2011.

Prieto, "Barriers, nephrotoxicology and chronic testing in vitro," Ahern Lab Anim. 2002, 30 Suppl 2:101-5.

Redfern, et al., "Impact and frequency of different toxicities throughout the pharmaceutical life cycle," The Toxicologist 2010, 114:231.

Rossol, et al., "LPS-induced cytokine production in human monocytes and macrophages," Crit Rev Immunol. 2011, 31(5):379-446.

Sabolic, et al., "Subchronic cadmium treatment affects the abundance and arrangement of cytoskeletal proteins in rat renal proximal tubule cells", Toxicol., 2001, 165(2-3):205-2016.

Saito, et al., "Present status and future perspectives on the development of bioartificial kidneys for the treatment of acute and chronic renal failure patients," Hemodial Int. 2011, 15(2):183-92.

Swerlick, et al., "Role of microvascular endothelial cells in inflammation," J Invest Dermatol. 1993, 100(1):111S-115S.

Szeto, et al., "Nephrotoxicity related to new therapeutic compounds," Ren Fail. 2005, 27(3):329-33.

Tang, et al., "Albumin stimulates interleukin-8 Expression in prosimal tubular epithelial cells in vitro and in vivo", J. Clin. Invest., 2003, 111(4):515-27.

Tang, et al., "Diabetic tubulopathy: an emerging entity," Contrib Nephrol. 2011, 170:124-34.

Tasnim, et al., "Effects of BMPs on Primary Human Renal Cells and the Generation of BMP-7-expressing Cells for Applications in Bioartificial Kidneys," Tissue Eng Part A 2012, 18:262-76.

Tramma, et al., "Interleukin-6 and interleukin-8 levels in the urine of children with renal scarring," Pediatr Nephrol. 2012, 27(9):1525-30.

(56) References Cited

OTHER PUBLICATIONS

Trayhurn, et al., "Secreted proteins from adipose tissue and skeletal muscle—adipokines, myokines and adipose/muscle cross-talk," Arch Physiol Biochem. 2011, 117(2):47-56.

Vesey, et al., "Isolation and primary culture of human proximal tubule cells," Methods Mol Biol. 2009, 466:19-24.

Waring, et al., "Earlier recognition of nephrotoxicity using novel biomarkers of acute kidney injury," Clin Toxicol (Phila) 2011, 49(8):720-8.

Wu, et al., "Multiplexed assay panel of cytotoxicity in HK-2 cells for detection of renal proximal tubule injury potential of compounds," Toxicol In Vitro 2009, 23(6):1170-8.

Yao, et al., "An in vitro method for the prediction of renal proximal tubular toxicity in humans", The Royal Society of Chemistry, 2013, vol. 2, pp. 352-365.

Zhang, et al., "In vitro cytotoxicity assay with selected chemicals using human cells to predict target-organ toxicity of liver and kidney," Toxicol In Vitro 2007, 21(4):734-40.

Zhang, et al., "Generation of easily accessible human kidney tubules on two-dimensional surfaces in vitro," J Cell Mol Med. 2011, 15(6):1287-98.

Zimmerhackl, et al., "Cadmium is more toxic to LLC-PK1 cells than to MDCK cells acting on the cadherin—catenin complex," Am J Physiol. 1998, 275(1 pt 2):F143-53.

International Search Report and Written Opinion mailed Dec. 4, 2013 in corresponding PCT application No. PCT/IB2013/001589.

Second Written Opinion mailed Jun. 27, 2014 in corresponding PCT application No. PCT/IB2013/001589.

International Preliminary Report on Patentability dated Sep. 18, 2014 and Response to 2nd Written Opinion filed Aug. 27, 2014 in corresponding PCT application No. PCT/IB2013/001589.

International Search Report and Written Opinion mailed on Jan. 22, 2014 in related PCT application No. PCT/IB2013/001944.

International Preliminary Report on Patentability issued on Jan. 20, 2015 in related PCT application No. PCT/IB2013/001944.

Office Action dated Nov. 27, 2015 in corresponding CN Patent Application No. 201380048888.

Extended European Search Report dated Nov. 23, 2015 in corresponding EP Patent Application No. 13820192.6.

Search Report and Written Opinion dated Nov. 12, 2015 in corresponding SG Patent Application No. 11201500367W.

Search Report and Written Opinion dated Nov. 17, 2015 in corresponding SG Patent Application No. 11201500370S.

First Office Action for corresponding Chinese Patent Application No. 201380048854.0, 20 pp. (including English translation), (Mar. 23, 2016).

Christian Koppelstaetter, et al., "Assessment of a New Cell Culture Perfusion Apparatus for In Vitro Chronic Toxicity Testing—Part 1: Technical Description", ALTEX, vol. 21, pp. 51-60, (Feb. 2004).

European Patent Office Communication enclosing Extended European Search Report for corresponding European Patent Application No. 13819944.3, 7 pp., (Feb. 22, 2016).

Maricke Kruidering, et al., "Cisplatin Effects on F-actin and Matrix Proteins Precede Renal Tubular Cell Detachment and Apoptosis In Vitro", Cell Death and Differentiation, vol. 5, pp. 601-614, (1998).

Alice Limonciel, et al., "Oxidative Stress Induced by Potassium Bromate Exposure Results in Altered Tight Junction Protein Expression in Renal Proximal Tubule Cells", Arch. Toxicol., vol. 86, pp. 1741-1751, (2012).

Agency for Sci, Tech & Research, Search Report and Written Opinion for Singaporean Patent Application No. 11201500367W, mailed Aug. 18, 2016.

Athelogou, et al., "Image Analysis for Calculation of the Toxicity Degree of Cells in Phase Contrast Microscopy Images", Bildverarbeitung für die Medizin 2011, Springer Berlin Heidelberg, (Mar. 13, 2011), 134-138.

Crawford, et al., "Toxicity in vital fluorescence microscopy: effect of dimethylsulfoxide, rhodamine-123, and dii-low density lipoprotein on fibroblast growth in vitro", in Vitro Cell Dev Biol., vol. 27, No. 8, (Aug. 1991), 633-638.

TABLE 1

| Compound | HPTC IC$_{50}$ | HK-2 IC$_{50}$ | LLC-PK1 IC$_{50}$ | Compound | HPTC IC$_{50}$ | HK-2 IC$_{50}$ | LLC-PK1 IC$_{50}$ |
|---|---|---|---|---|---|---|---|
| 1 | >1000 | >1000 | >1000 | 22 | >1000 | >1000 | ND |
| 2 | >1000 | >1000 | >1000 | 23 | >1000 | >1000 | >1000 |
| 3 | 707 | 632 | 795 | 24 | >1000 | >1000 | >1000 |
| 4 | >1000 | ND | >1000 | 25 | >1000 | >1000 | >1000 |
| 5 | >1000 | ND | ND | 26 | 742 | 678 | 945 |
| 6 | 47 | 94 | 38 | 27 | >1000 | >1000 | >1000 |
| 7 | ND | >1000 | 469 | 28 | >1000 | >1000 | >1000 |
| 8 | ND | ND | ND | 29 | >1000 | >1000 | >1000 |
| 9 | >1000 | >1000 | >1000 | 30 | >1000 | >1000 | >1000 |
| 10 | >1000 | >1000 | 69 | 31 | >1000 | >1000 | >1000 |
| 11 | 21 | 7 | 19 | 32 | >1000 | ND | >1000 |
| 12 | >1000 | >1000 | >1000 | 33 | >1000 | >1000 | >1000 |
| 13 | 4 | ND | 9 | 34 | >1000 | >1000 | >1000 |
| 14 | 147 | 116 | 79 | 35 | >1000 | >1000 | >1000 |
| 15 | >1000 | ND | >1000 | 36 | >1000 | >1000 | >1000 |
| 16 | 96 | ND | ND | 37 | >1000 | >1000 | >1000 |
| 17 | >1000 | ND | >1000 | 38 | >1000 | >1000 | 71 |
| 18 | 23 | 14 | ND | 39 | >1000 | >1000 | >1000 |
| 19 | 45 | 44 | 45 | 40 | >1000 | >1000 | >1000 |
| 20 | >1000 | >1000 | ND | 41 | >1000 | >1000 | >1000 |
| 21 | ND | ND | ND | | | | |

FIGURE 8

IN VITRO ASSAY FOR PREDICTING RENAL PROXIMAL TUBULAR CELL TOXICITY

CROSS-REFERENCE TO RELATED APPLICATIONS

This patent application is a U.S. National Phase Application under 35 U.S.C. §371 of International Application No. PCT/IB2013/001589, filed on Jul. 22, 2013, entitled IN VITRO ASSAY FOR PREDICTING RENAL PROXIMAL TUBULAR CELL TOXICITY, which claims benefit of, and priority from, U.S. provisional application No. 61/674,024, filed on Jul. 20, 2012, the contents of which were incorporated by reference.

FIELD OF THE INVENTION

The present invention relates to in vitro assay methods for predicting the toxicity of a compound for renal proximal tubular cells, including predicting toxicity in vivo.

BACKGROUND OF THE INVENTION

The kidney is one of the major target organs for drug-induced toxicity. Nephrotoxic drugs and chemicals can induce acute kidney injury (AKI), or chronic kidney disease and subsequently end stage renal disease (ESRD) (1-3). AKI and ESRD patients have increased morbidity and mortality and depend on dialysis (1, 4, 5). About 5% of all hospitalized patients and ~20%-30% of ICU patients develop AKI, and ~20%-25% of these cases are due to nephrotoxic drugs (2-4). When alternative and new drugs become available their nephrotoxic potential is often underestimated (6), which leads again to clinical complications, as in case of COX2 inhibitors (7).

Typically, nephrotoxicity is detected only late during drug development and accounts for 2% of drug attrition during pre-clinical studies and 19% in phase 3 (8). Also, due to the large functional reserve of the kidney nephrotoxic effects often become obvious only after regulatory approval. A recent example is tenofovir, which injures the renal proximal tubules (9, 10). Together, the problems outlined above are associated with increased risks for patients and subjects enrolled in clinical trials as well as substantial costs for the health care system and the pharmaceutical industry.

One major problem is the lack of pre-clinical models with high predictability. The predictability of animal models is compromised by interspecies variability, and there are other problems such as high costs and low throughput. Further, legislation changes in the EU (REACH and the $7^{th}$ Amendment of the Cosmetics Directive) and new initiatives in the USA (ToxCast and Tox21) have increased the interest in in vitro models. Regulatory accepted or validated in vitro models for the prediction of nephrotoxicity in humans are currently not available. Major difficulties are related to the identification of appropriate cell types and endpoints (11-13).

In the kidney the cells of the renal proximal tubule (PT) are a major target for drug-induced toxicity due to their roles in glomerular filtrate concentration and the transport of drugs and organic compounds (2, 3). PT-derived cell lines, such as the human and porcine cell lines HK-2 (human kidney-2) and LLC-PK1 (Lewis lung cancer-porcine kidney 1), have been frequently applied in in vitro nephrotoxicology. However, immortalized cells are less sensitive than human primary renal proximal tubular cells (HPTC) (14) and insensitive to well-known nephrotoxicants (13), which is due to do functional changes and changes in drug transporter expression associated with immortalization (15-17). Further, endpoints that are associated with general cytotoxicity, such as cell death, metabolic activity or ATP depletion, are not useful for addressing organ-specific toxicity. A recent study measuring ATP-depletion in liver-, kidney PT- and heart-derived cell lines treated with hepatotoxic, nephrotoxic and cardiotoxic compounds found that the majority of compounds had similar effects in all three cell lines (18).

The European and US regulatory agencies in charge of the validation and acceptance of alternative methods (European Centre for the Validation of Alternative Methods (ECVAM) and the National Toxicology Program Interagency Center for the Evaluation of Alternative Toxicological Methods/Interagency Coordinating Committee on the Validation of Alternative Methods (NICEATM/ICCVAM)) are currently not involved in any activities on the validation of methods for in vitro nephrotoxicology. The ECVAM has funded one pre-validation study (19) which used 15 drugs. Other models for in vitro nephrotoxicology that have been developed since then during the last 10 years (20-24) have been tested with limited numbers of drugs and are of unclear predictability. A recently developed high-throughput mitochondrial nephrotoxicant assay is based on rabbit cells (25), which raises issues concerning interspecies variability. This applies also to a model employing PT freshly isolated from murine kidneys (23, 24). Both models would still require the use of animals.

SUMMARY OF THE INVENTION

In one aspect, the invention provides an in vitro method of screening for renal proximal tubular toxicity of a compound. The method comprises contacting a test compound with a test population of renal proximal tubular cells; and examining one or more cell morphology features, examining one or more cytoskeleton features, and/or determining cell numbers of the renal proximal tubular cells in the test population; and comparing cell morphology, arrangement of cytoskeletal components and/or cell count of the test population with cell morphology, arrangement of cytoskeletal components and/or cell count of a control population that has not been contacted with the test compound; wherein a change in one or more cell morphology features, a change in arrangement of one or more cytoskeleton features or a decrease in cell numbers of the test population relative to the control population is indicative that the test compound is toxic for renal proximal tubular cells.

The change in morphology features may comprise one or more of an increase in rounding of the proximal tubular cells, a decrease in cell area, and an increase in nucleus:whole cell ratio. The change in arrangement of cytoskeleton features may comprise a change in arrangement of one or both of F-actin and tubulin.

The method may further comprise, prior to the examining and/or the determining, labeling the test population with a detectable label, and/or labeling the control population with the detectable label. The detectable label may be a fluorescent label or a coloured label. The detectable label may be a nuclear label, a whole cell label, a cytoplasmic label, a label for cytoskeletal proteins or a cell surface label.

In the method, the renal proximal tubular cells may be derived from somatic cells or from stem cells, including for example primary cells or are cells from a stable cell line. For example, the renal proximal tubular cells may derived from somatic cells, and may be human primary renal proximal tubular cells, HK-2 cells, or LLC-PK1 cells. For example, the renal proximal tubular cells may be derived from stem cells, and may be differentiated from embryonic stem cells, mesenchymal stem cells, or induced pluriopotent stem cells. In some embodiments, the renal proximal tubular cells are human renal proximal tubular cells. In some embodiments, the renal proximal tubular cells are non-human renal proximal tubular cells.

In the method, the contacting may be performed over a period of time, for example for about 8 hours or longer. The contacting may be contacting is repeated one or more times in a period of from about 3 to about 14 days. The contacting may comprise adding the test compound to the test population of renal proximal tubular cells at a concentration of about 0.001 to about 1000 µg/ml.

Other aspects and features of the present invention will become apparent to those of ordinary skill in the art upon review of the following description of specific embodiments of the invention in conjunction with the accompanying figures and tables.

BRIEF DESCRIPTION OF THE DRAWINGS

The figures, which illustrate, by way of example only, embodiments of the present invention, are as follows.

FIG. 8. (Table 1) Comparison of drug effects on cell numbers. HPTC (ATCC), HK-2 and LLC-PK1 cells were exposed to the 41 test compounds at concentrations ranging from 1 µg/ml-1000 µg/ml. $IC_{50}$ values were calculated based on cell numbers determined by HCS. A value of >1000 µg ml-1 was assigned if cell viability was >50% at the highest concentration of a compound (1000 µg ml-1). Cell numbers were not determined (ND) in some cases. Compounds 1-22 are nephrotoxic in humans and damage directly the renal proximal tubule. Compounds 23-33 are nephrotoxic in humans, but do not damage directly the renal proximal tubule. Compounds 34-41 are non-nephrotoxic in humans.

DETAILED DESCRIPTION

Figure 1:
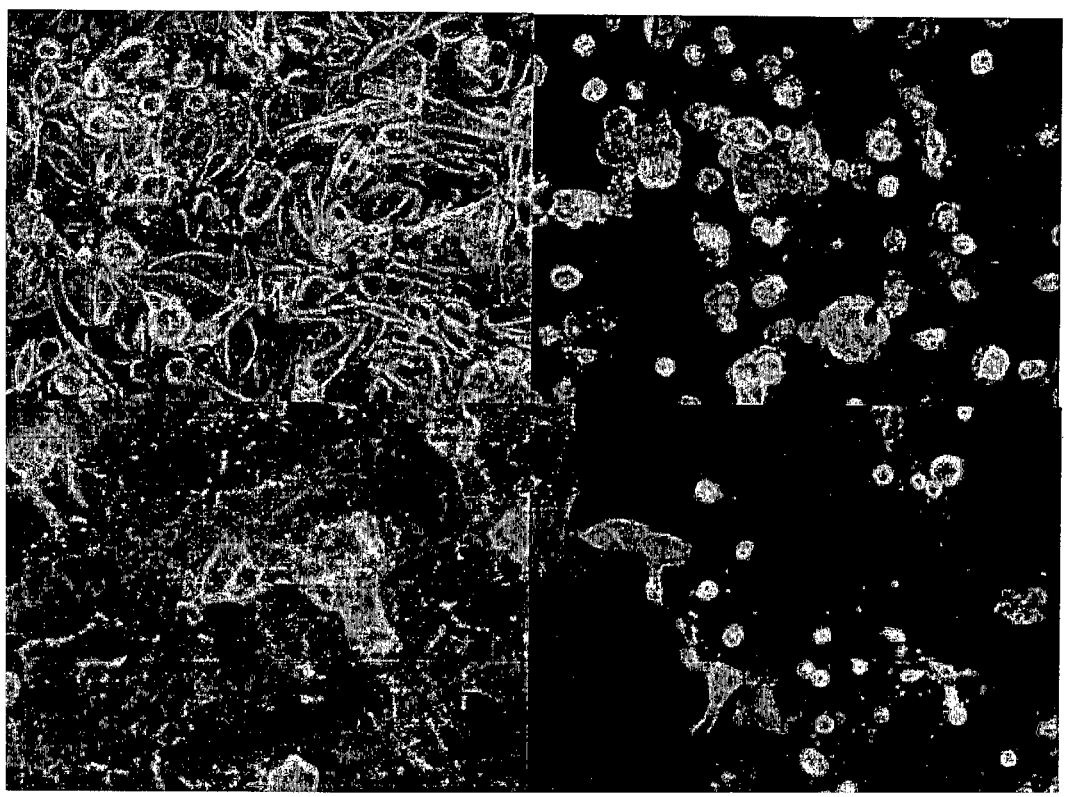
FIG. 1. Top panels: Commercial HPTC (American Type Culture Collection); bottom panels: HPTC isolated from fresh human kidney samples. Cells were left untreated (left-hand panels) or treated with 0.2 mg/ml of tetracycline (top right-hand panel) or gentamicin (bottom right-hand panel). Treatment with these nephrotoxins led to morphological changes (green: F-actin) and a decrease in cell numbers as indicated by the decrease in the number of cell nuclei (blue). Such changes are quantifiable by HCS and subsequent image analysis.

There is provided an in vitro assay using cultured renal proximal tubular cells (PTC), including human primary renal proximal tubular cells (HPTC) or PTC-like cells derived from stem cells to predict proximal tubular toxicity of a compound in vivo. The assay is based on various morphological, cytoskeletal and cell number changes observed in the PTC or PTC-like cells that indicate renal proximal tubular (PT) toxicity.

It was observed that when treated with compounds that are nephrotoxins that directly damage PTC, the PTC tend to undergo morphological changes, including cell rounding and decrease in cell area, and also tend to undergo rearrangements of cytoskeletal components such as F-actin or microtubuli. Cell numbers often decrease upon cell death in response to PT-damaging nephrotoxic compounds, as can be measured by counting the number of cell nuclei in a culture of PTC upon treatment with a PT-specific nephrotoxin.

Thus, there is provided a method of screening for the PT-specific toxicity of a compound. Briefly, the method comprises contacting a test population of PTC with a test compound that is to be assessed for PT-specific toxicity. Subsequent to the contacting, one or more features of the test population is examined, for example cell morphology, arrangement of cytoskeletal components or cell number, and the characteristics of the feature or features of the test population are compared to the characteristics of the same feature or features of a control population of PTC that has not been contacted with the test compound, although the control population will typically be contacted with a vehicle control. If the feature or features of the test population differs from the feature or features of the control population, the indication is that the test compound is a PT-specific toxin that damages PTC.

The cells used in the method, both for the test population and control population of cells, may be any type of PTC, or may be any type of PTC-like cells that have been differentiated from stem cells. The cells may be from any species that has renal proximal tubular cells, including a mammal, such as a pig or a human.

Thus, the cells may be derived from somatic cells. The cells may be from an established renal proximal tubular cell line, or may be primary renal proximal tubular cells. For example, the cells may be primary PTC isolated from kidney samples, including PTC isolated from a human kidney. The cells may be primary PTC obtained from a commercial source, including for example the American Type Culture Collection (ATCC). The cells may be an established renal proximal tubular cell line, including for example human kidney (HK)-2 cells or porcine LLC-PK1 cells.

In particular embodiments, the cells are human renal proximal tubular cells, either primary human renal proximal tubular cells (HPTCs) or from an established cell line.

Alternatively, the cells may be renal proximal tubular cell-like (PTC-like) cells differentiated from stem cells, including embryonic stem cells, adult stem cells such as mesenchymal stem cells, or induced pluripotent stem cells. PTC-like cells are cells that have been differentiated to express certain renal proximal tubular cell markers such as aquaporin (AQP)-1, which possess water transport functionality, CD13 (aminopeptidase N) and kidney-specific cadherin. PTC-like cells form differentiated and polarized epithelia sealed by tight junctions in vitro and generate tubular structures in vitro and in vivo. They display enzymatic functions typical for PTC and respond to parathyroid hormone. A method to differentiate stem cells into renal proximal tubular cell-like cells is published, for example in WO 2009/011663 and in Narayanan et al. (26). Commercially available stem cell lines may be used, including for example human embryonic stem (HUES-7) cells.

In some instances, HPTC may be affected by inter-donor variability or may be difficult to obtain. Further, HPTC in vitro may often display a certain degree of de-differentiation, which possibly reflects an injury-like state after cell isolation and could explain the lack of substantial up-regulation of novel AKI biomarkers after exposure to PT-specific nephrotoxins that may be observed. The use of stem-cell derived renal proximal tubular-like cells in some embodiments may avoid some or all of the issues using HPTCs.

As used throughout this disclosure, reference to renal proximal tubular cells or PTC is intended to include reference to renal proximal tubular cell-like (PTC-like) cells that have been differentiated from stem cells, where context allows.

As will be appreciated, the same cell type should be used for the test population and control population.

As used herein, the term "cell" when referring to a renal proximal tubular cell or a renal proximal tubular-like cell is intended to refer to a single cell as well as a plurality or population of cells. Similarly, the term "cells" is also intended to refer to a single cell, where context allows.

Thus, in the method, cells are first cultured, in accordance with standard tissue culture methods. Methods for culturing are also described in the following Examples. Tissue culture conditions and techniques for renal proximal tubular cells are known. It should be noted that high serum concentrations in tissue culture medium may have an effect of causing the cells to de-differentiate. Thus, it may be advantageous to limit serum concentration in the tissue culture medium, for example to about 0.5% serum or less.

Since morphological changes may be detected, cells should be grown attached to a support. The cells may be grown on a tissue culture substrate, such as a plate or in a well of a multi-well plate. It should be noted that favourable results may be obtained when the cells are cultivated on tissue culture grade polystyrene rather than more compliant membranes such as transwell inserts.

For example, cells may be seed at high density (e.g. 50 000 cells/cm$^2$) in multi-well plates. The tissue culture polystyrene typically does not need any treating with a coating, gel etc. The cells may be cultivated for 3 days prior to contacting with the compound in order to provide the cells time to form a differentiated epithelium, which would be in the form of a confluent monolayer epithelium (as opposed to sub-confluent or multi-layered that may be used in other embodiments). Contacting with the test compound may then be performed overnight, for example for between about 8 hours and 16 hours, or even longer. An example of suitable culture conditions is provided for example in Li et al., *Tox. Res*, 2013 (DOI: 10.1039/c3tx50042j).

In some embodiments, the cells are grown in a monolayer, such as a confluent or subconfluent monolayer, which may assist with visualization of morphological traits, particularly if high content screening methods are used. It should be noted that at cell densities of confluent monolayers, good cell differentiation can be achieved.

In the method, the in vitro cultured cells are contacted with a compound that is to be tested for toxicity to PTC in vivo.

The test compound may be any compound that is to be assessed for PT-specific toxicity. The test compound may be any compound that is expected to come into contact with a subject, including being absorbed or ingested by a subject. For example, the test compound may be a pharmaceutical compound, an organic compound, a pesticide, an environmental toxin, a heavy metal-containing compound, an organic solvent, a food additive, a cosmetic or a nanoparticle.

The contacting may be done by adding the compound to the tissue culture medium in which the cells are cultured.

The contacting may be done over a period of time, for example by incubating the compound that is to be tested with the cells in culture. The contacting may be performed for about 8 hours or longer, for about 16 hours or longer, for 24 hours or longer, for 72 hours or longer.

The concentration of the test compound to be used may be varied, and may depend on the compound that is to be tested. Typically, when toxicity is observed in vitro in PTC at concentrations from about 1 µg/ml to about 1000 µg/ml, such toxicity may tend to be predictive of PTC toxicity in vivo at clinically relevant concentrations. As set out in the Examples below, test compounds 1-22 display PT-specific toxicity in humans at clinically relevant concentrations.

For example, the test compound may be contacted with the population of cells at a concentration of about 0.001 µg/ml or higher, about 0.01 µg/ml or higher, about 0.1 µg/ml or higher, about 1 µg/ml or higher, about 10 µg/ml or higher, about 100 µg/ml or higher, or about 1000 µg/ml or higher. The test compound may be contacted with the population of cells at a concentration of from about 0.001 µg/ml to about 1000 µg/ml, from about 0.005 µg/ml to about 1000 µg/ml, or from about 0.01 µg/ml to about 500 µg/ml.

As will be appreciated, the control population of renal proximal tubular cells, although not contacted with the test compound, may be contacted with a negative control solution, for example the solvent or solution used to dissolve the test compound for contacting with the test population (vehicle control).

The contacting may be repeated. For example, the contacting may be performed two or more times, three or more times, four or more times or five or more times over a given period of time.

For example, after the first period of contacting is completed, the tissue culture medium may be replaced with fresh medium that contains the compound. Alternatively, the medium may be replaced with fresh medium that does not contain the test compound, and after a period of time with no contact, the test compound may then again be contacted with the test population of cells.

The contacting thus may be repeated one or more additional times (beyond the first instance of contacting), for example over a period of about 3 to about 14 days. The interval without any contact of test compound (i.e. exposing the cells to fresh medium) may last, for example, for one day to 14 days between the periods of contacting.

The contacting may be repeated shortly before or immediately before repeated prior to the examining for morphological or cytoskeletal features or the determining of cell numbers.

In order to assist with examining the test population, as well as the control population, the cell populations may both be labelled with a detectable label. A detectable label is any label or marker that can be detected using visualization methods, including for example a fluorescent label or a coloured label.

The detectable label may label the whole cell, exterior surface of the cell, the cytoplasm or structures or molecules within the cytoplasm, the nuclear membrane, the nucleus or structures or molecules within the nucleus including DNA.

In one example, the label may be a fluorescent dye or a coloured dye that is detectable by fluorescence microscopy or by phase contrast microscopy. The fluorescent dye or coloured dye may have an affinity for a particular region or structure within the cell. In another example, the label may be an antibody directed against a molecule found in a particular location within a cell, which antibody may itself be labelled with a fluorescent dye or coloured dye. The antibody may be directed against the whole cell, a cell surface marker, a molecule located within the nucleus or a molecule located within the cytoplasm. For example, the detectable label may be an antibody directed against alpha- or beta-tubulin, which may be conjugated with a fluorochrome or which may be detected using a secondary antibody that is fluorescently labelled. The detectable label may be, for example, 4',6'-diamidino-2'-phenylindole hydrochloride (DAPI; DNA dye), a nucleic acid stain such as Hoechst nucleic acid stains (e.g. Hoechst 33258), Whole Cell Stain™ (Cellomics, commercial), phalloidin (labels F-actin, and may be directly conjugated to a fluorochrome like rhodamine), DiI (CAS number 41085-99-8; membrane stain) or DiO (CAS number 34215-57-1; membrane stain).

In some embodiments, two or more labels may be used for the examining stage. For example, one label directed to the cell surface or perimeter may be used together with a second label directed to the nucleus.

The labelling may be achieved using standard methods for cell visualization, for example by adding a dye or labelled antibody to the cell culture that is to be examined.

After the contacting with the test compound, the test population is examined for one or more morphological features, arrangement of one or more cytoskeletal features and/or to determine cell number.

The test population may be examined for morphological features such as cell roundness, cell area, and an increase in nucleus:whole cell ratio.

As well, the test population may be examined for arrangement of cytoskeleton features such as arrangement of F-actin or tubulin structures such as microtubuli.

Upon exposure to a PT-specific nephrotoxic compound, the spreading of the cell may decrease, leading to an overall decrease in cell area. As well, the ratio of the area of the nucleus:the area of the entire cell (nucleus:whole cell ratio) may thus correspondingly increase. Thus, whole cell area and/or the area of the nucleus may be calculated by measuring the dimensions of the cell, or if high content screening is used, the number of pixels in the relevant region of the cell.

As well, upon exposure to a PT-specific nephrotoxic compound, cells may undergo rounding. Thus, the method may include determining the roundness of cells after exposure to the test compound. For example, roundness values may be calculated based on cell area and diameter, as $(4 \times area)/(\pi \times diameter^2)$. Using this formula, a cell that is not at all round (e.g. elongated with a long and thin shape) will have a measurement of 0 or approaching 0, whereas a cell that is completely circular in the x,y plane will have a measurement of 1.

Simultaneously with the morphological changes that a renal proximal tubular cell toxin may induce in the cells, the arrangement of certain cytoskeletal structural elements of the cell may also be altered. For example, changes in the arrangement of actin fibers as well as microtubuli have now been found to correlate with PT-specific toxicity in the method. Thus, the arrangement of F-actin or tubulin may be examined. By specifically staining cells for F-actin or tubulin, the pattern of actin fibers or microtubules and non-polymerized tubulin can be visualised. Such cytoskeletal changes may be related to changes in cell area and roundness. Changes in multiple features can be addressed simultaneously by multivariate performance measures, for example by assessing Haralick texture features. Commercial software programs are available to perform such measurements and calculations.

PT-specific nephrotoxic compounds may also reduce the number of intact cells in the test population. Thus, the number of cells can be counted. For example, cell numbers can be determined by counting of intact nuclei in the cell population, or based on counting whole cell bodies.

As can be seen from the above description, the use of computer-assisted detection techniques may assist in examining the morphological features, arrangement of cytoskeletal components and cell number. Thus, techniques such as high content screening may be used to visualize and examine the morphological features, arrangement of cytoskeletal components and cell numbers of the test population. High content screening techniques are known and used in the art. Such techniques may involve automated image analysis to assess phenotypes, including of whole cells, cellular structures and nuclei, and typically involve high resolution microscopes and automated data collection and analysis. The assay may be performed using robotic or automated devices in order to increase speed. Multiple parameters may be assessed for a given cell population simultaneously, further increasing the speed and throughput of the assay.

Once assessed, the examined morphological features and/or cytoskeletal features and/or cell numbers obtained for the test population is compared with the values obtained for the control population of PTC under the same conditions minus the contact with the test compound. A change in one or more of these features in the test population relative to the control population is indicative that the test compound is a nephrotoxin that is directly toxic for renal proximal tubular cells. Thus, one or more of a decrease in cell number, a decrease in cell area, an increase in cell rounding, a change in F-actin and/or tubulin arrangement and an increase in nucleus:whole cell ratio can be seen to indicate that the test compound is a nephrotoxin that directly damages renal proximal tubular cells.

It may be desirable to set a threshold level for each of the morphological parameters and/or cell number. This may be done by using positive and negative control populations, as well as a set of compounds that are known to be non-toxic, a set of compounds that are known to be nephrotoxic but not specifically toxic to renal proximal tubular cells, and a set of compounds that are known to be specifically toxic to renal proximal tubular cells. Major performance metrics can be calculated such as the positive and negative predictive values. Selectivity and sensitivity can be determined based on the numbers of true positives, false positives, true negatives and false negatives, which were determined by the measuring morphological and cytoskeletal features and cell numbers for controls and each set of compounds. The predictability of the method can be further determined by plotting receiver operating characteristic curves (ROC) and calculating the area under the curve values. Such ROC analysis methods are known and used in the art.

Additionally or alternatively to using threshold levels to determine toxicity, statistical analysis can be performed comparing the results from the test population with those of the control population. Differences between the results for both populations that are determined to be statistically significant would be seen to indicate a positive result, i.e. that the test compound is a nephrotoxin that specifically damages PTC.

For any given test compound a dose response curve may be calculated by testing the compound at increasing concentrations and comparing the results for each concentration to results for a control population. In this way, an $EC_{50}$ or $IC_{50}$ value may be obtained for test compounds that are found to be toxic to renal proximal tubule cells.

Thus, the methods described herein may be useful to predict compounds that will be toxic for PTC in humans at clinically relevant concentrations of the compound. As indicated above, compounds 1-22 described in the following Examples (see FIG. 8) indicated positive PCT-specific toxicity at concentrations that are known to be clinically relevant based on previous known studies. Such predictive strength may be seen for compounds tested in the concentration range of from about 1 µg/ml to 1000 µg/ml in vitro.

The methods as described herein are further exemplified by way of the following non-limiting examples.

EXAMPLES

Example 1

It was observed that human primary renal proximal tubular cells (HPTC) show substantial changes in cell morphology when treated with nephrotoxins (see FIG. 1). Also, reduced cell numbers are observed due to cell death. This assay uses cell nuclei count and changes in cell morphology, such as cell area and roundness to assess toxicity on HPTC First, cells were seeded into multi-well plates and cultured for 3 days. They were then exposed to a test compound for 16 hours. Cells used were commercial HPTC (American Type Culture Collection; "ATCC") and HPTC isolated by the inventors from fresh human kidney samples.

Cells were left untreated or treated with 0.2 mg/ml of tetracycline (ATCC cells) or gentamicin (inventor's isolates).

Next, cells were fixed and stained, using both nuclear staining and F-actin detection. Treatment with these nephrotoxins led to morphological changes as indicated by F-actin arrangement, decrease in cell area, increase in cell roundness and a decrease in cell numbers as indicated by the decrease in the number of cell nuclei (FIG. 1).

Such changes are quantifiable by HCS and subsequent image analysis. The plates are screened with HCS and subsequent image analysis was performed.

Example 2

This example was performed using commercial HPTC (ATCC).

Cells were seeded into multi-well plate and cultured for 3 days. Cells were then left untreated or treated with gentamicin (2.5 mg/ml), $CdCl_2$ (10 µg/ml), aristolochic acid (100 µg/ml), cisplatin (100 µg/ml) or DMSO (50 µg/ml).

Figure 2:
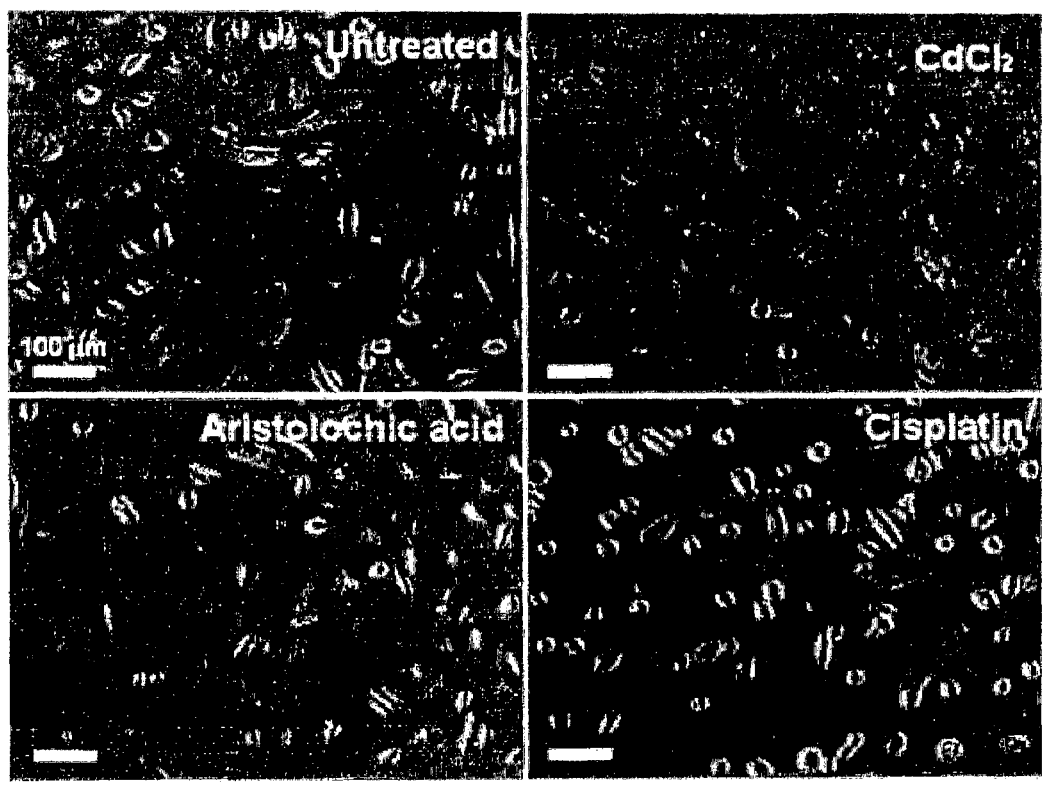
FIG. 2. HPTC (ATCC) were seeded into multi-well plates, cultured and then left untreated or treated with $CdCl_2$ (10 µg/ml), aristolochic acid (100 µg/ml) or cisplatin (100 µg/ml). Cells were imaged using phase contrast microscopy.

After 24 hrs, cells were imaged by phase contrast microscopy (FIG. 2; gentamicin image and DMSO image not shown).

Example 3

Various renal proximal tubular cell types were used: HPTC (ATCC), LLC-PK1 cells and HK-2 cells.

Figure 3:
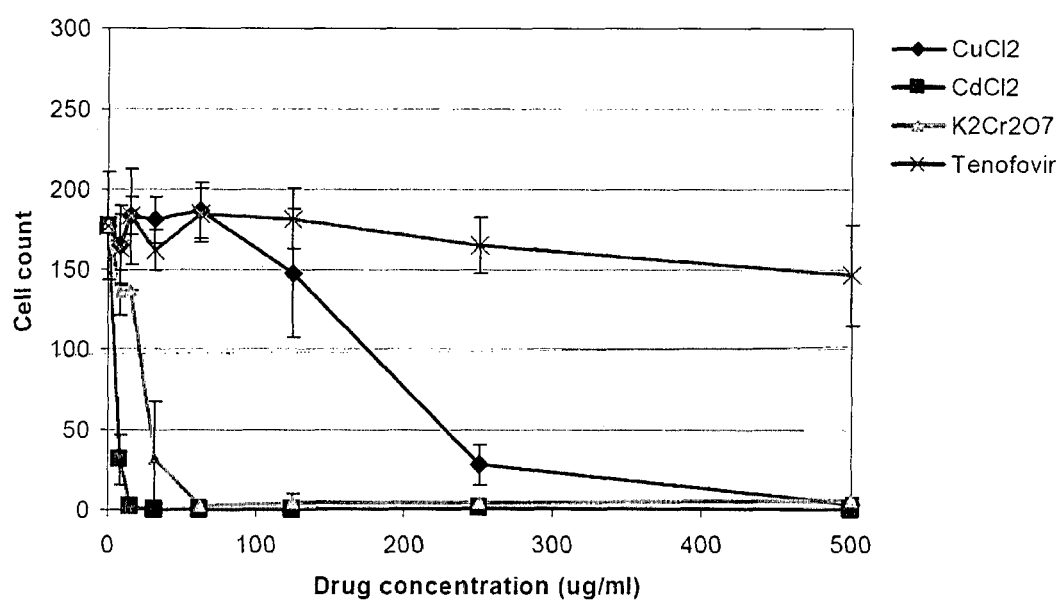
FIGS. 3 to 7. HPTC (ATCC) (FIG. 3), LLC-PK1 cells (FIGS. 4 and 6) and HK-2 cells (FIGS. 5 and 7) were seeded into multi-well plates, cultured and then left untreated or treated with up to 500 µg/ml of $CuCl_2$, $CdCl_2$, $K_2Cr_2O_7$ or tenofovir (FIGS. 3 to 5) or gentamicin, tetracycline, 5-fluorouracil or $As_2O_3$ (FIGS. 6 and 7). Cell nuclei were stained with DAPI and cells were imaged and counted by high content screening (HCS) methods.
Figure 4:
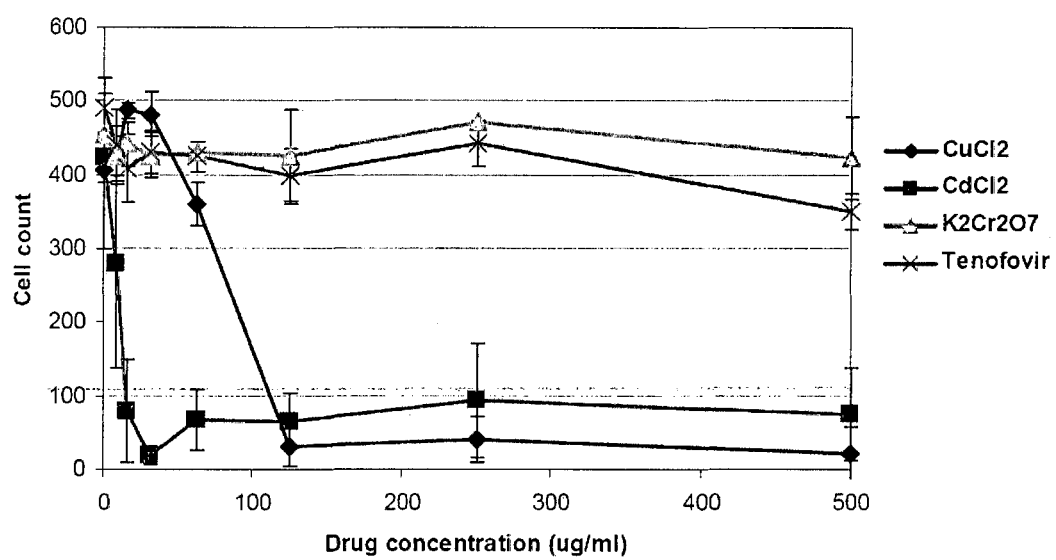
Figure 5:
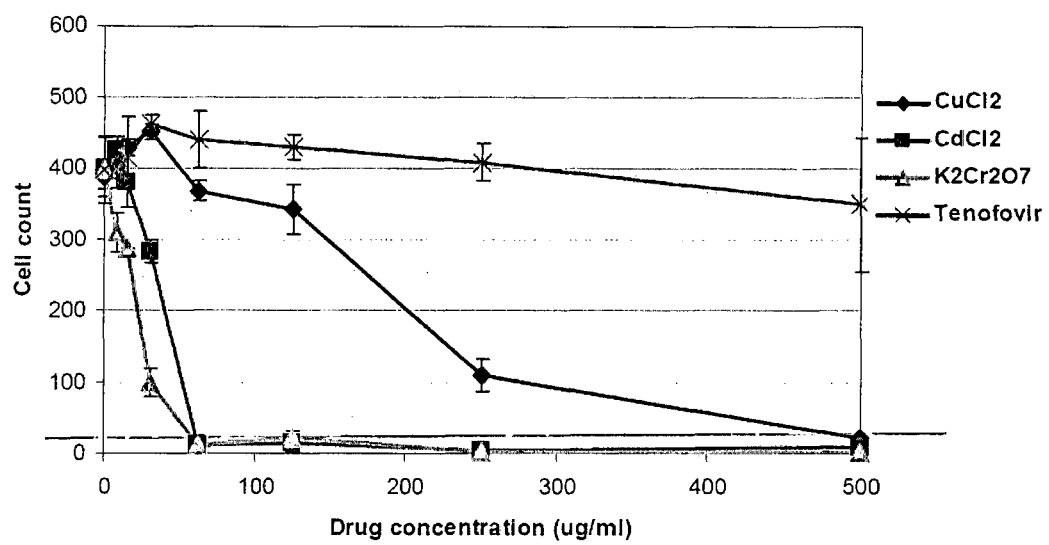
Figure 6:
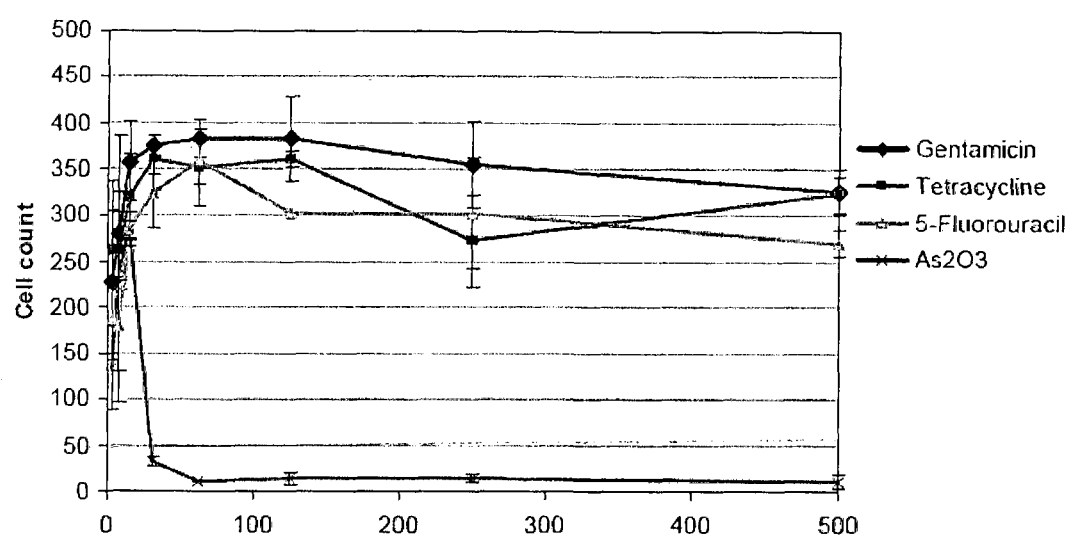
Figure 7:
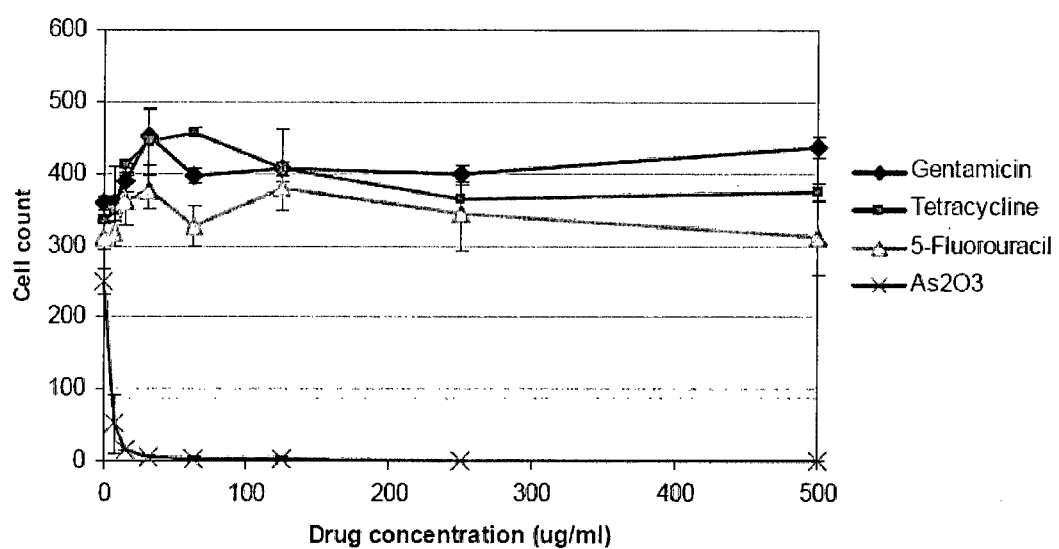

Cells were cultured and treated as described in Example 2, using from 0 to 500 µg/ml of $CuCl_2$, $CdCl_2$, $K_2Cr_2O_7$ or tenofovir (FIGS. 3 to 5) or gentamicin, tetracycline, 5-fluorouracil or $As_2O_3$ (FIGS. 6 and 7). Cells were stained, imaged and counted. The different types of PTC responded differently to the compounds and HPTC were most sensitive (FIGS. 3-5).

Example 4

The effect of varying concentrations of test compounds on the viability of HPTC, HK-2 cells and LLC-PK1 cells was assessed and $IC_{50}$ values were determined for each compound. $IC_{50}$ values were calculated based on cell numbers determined using high content screening. A value of >1000 µg/ml was assigned if cell viability was more than 50% at the highest concentration tested for the relevant compound (1000 µg/ml). In some cases, cell numbers were not determined (ND).

The results are shown in Table 1 (FIG. 8). Compounds 1-41 are, respectively: 1 Gentamicin, 2 Tobramycin, 3 Rifampicin, 4 Tetracycline, 5 Puromycin, 6 Cephalosporin C, 7 5-Fluorouracil, 8 Cisplatin, 9 Ifosfamide, 10 Paraquat, 11 Arsenic(III) oxide, 12 Bismuth(III) oxide, 13 Cadmium (II) chloride, 14 Copper(II) chloride, 15 Germanium(IV) oxide, 16 Gold(I) chloride, 17 Lead acetate, 18 Potassium dichromate, 19 Tacrolimus, 20 Cyclosporin A, 21 Citrinin, 22 Tenofovir, 23 Vancomycin, 24 Phenacetin, 25 Acetaminophen, 26 Ibuprofen, 27 Furosemide, 28 Lithium chloride, 29 Lindane, 30 Ethylene glycol, 31 Valacyclovir, 32 Lincomycin, 33 Ciprofloxacin, 34 Ribavirin, 35 Glycine, 36 Dexamethasone, 37 Melatonin, 38 Levodopa (DOPA), 39 Triiodothyronine, 40 Acarbose and 41 Atorvastatin. Compounds 1-22 are nephrotoxic in humans and damage directly the renal proximal tubule. Compounds 23-33 are nephrotoxic in humans, but do not damage directly the renal proximal tubule. Compounds 34-41 are non-nephrotoxic in humans.

Example 5

HPTC were assessed for cell rounding and a decrease in cell area upon exposure to bismuth (III) oxide or 10% DMSO (positive control). Water was used as a negative vehicle control.

Figure 9:
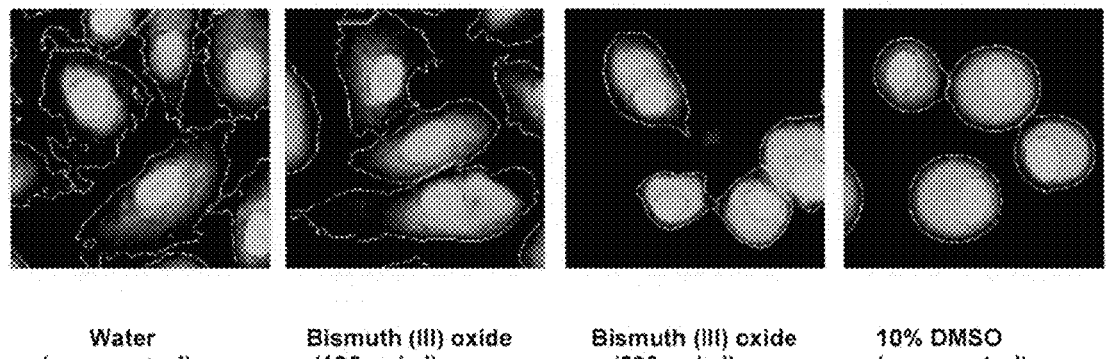
FIG. 9. Micrographs of HPTC exposed to the vehicle control (vehicle: water), bismuth (III) oxide or 10% DMSO (positive control).

Cells were exposed to water (vehicle control), 125 µg/ml bismuth (III) oxide, 500 µg/ml bismuth (III) oxide or 10% DMSO for 12 hours. Cells were stained with DAPI (blue) and Whole Cell Stain (green; Cellomics) (FIG. 9) and then measured for roundness and cell area.

Example 6

Figure 10:
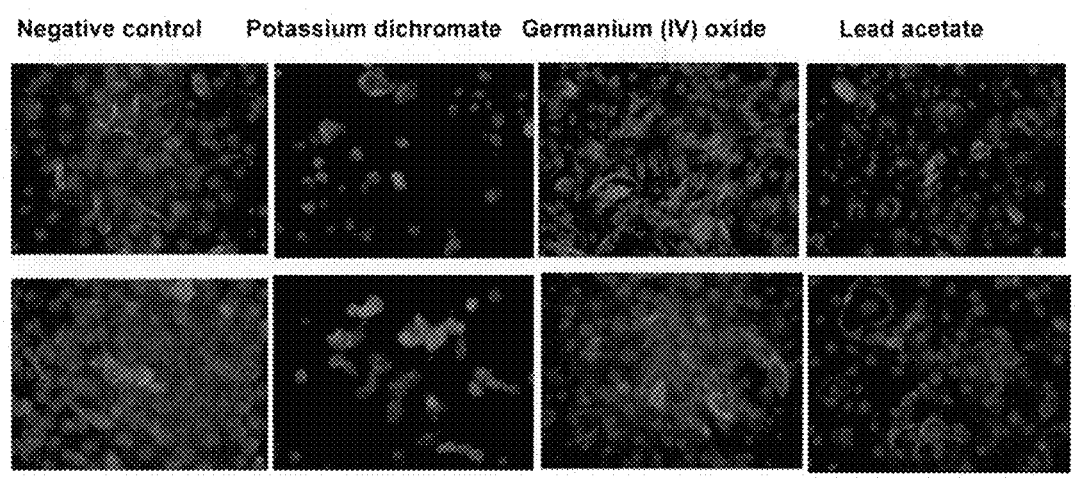
FIG. 10. Micrographs of HPTC that were left untreated (negative) control, or that were exposed to potassium dichromate, germanium (IV) oxide or lead acetate at concentrations of 1000 µg/ml (upper row) or 500 µg/ml (lower row). Red: F-actin, blue: cell nuclei.
Figure 11:
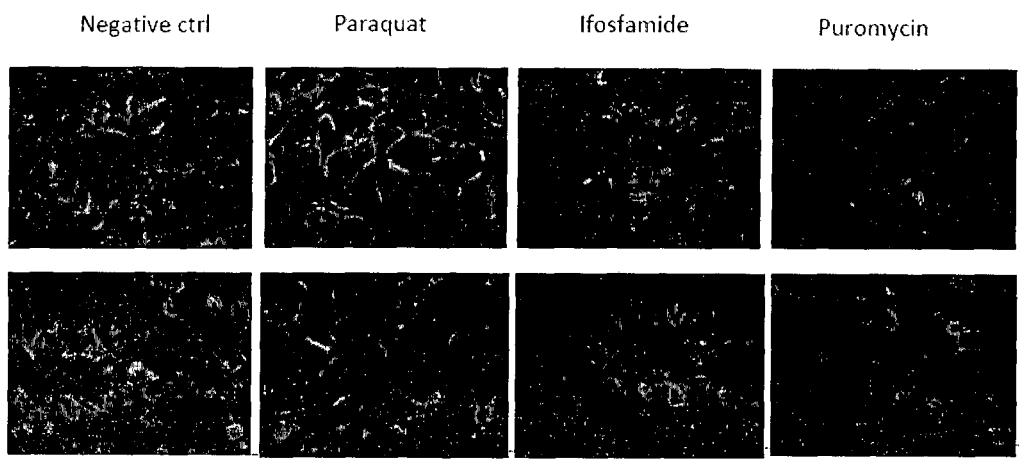
FIG. 11. Micrographs of HPTC that were left untreated (negative) control, or that were exposed to paraquat, ifosfamide or puryomycin at concentrations of 1000 µg/ml (upper row) or 500 µg/ml (lower row). Red: F-actin, blue: cell nuclei.
Figure 12:
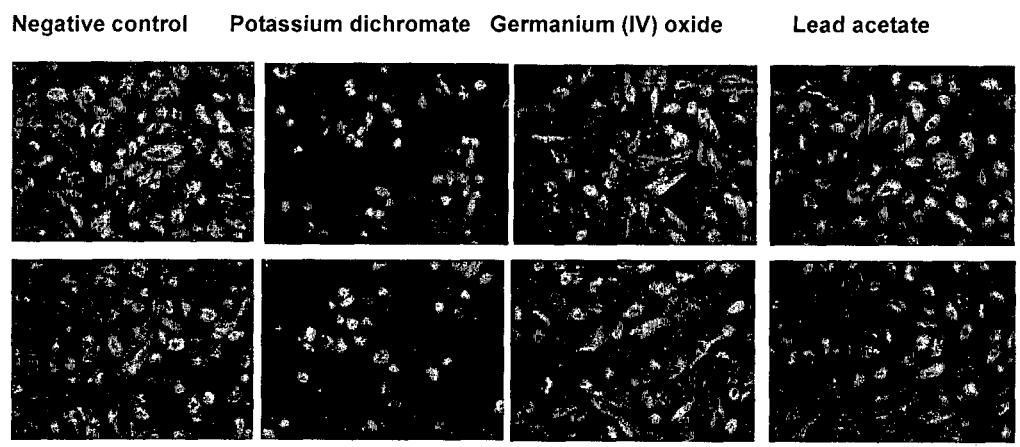
FIG. 12. Micrographs of HPTC that were left untreated (negative) control, or that were exposed to potassium dichromate, germanium (IV) oxide or lead acetate at concentrations of 1000 µg/ml (upper row) or 500 µg/ml (lower row). Green: alpha-tubulin, blue: cell nuclei.
Figure 13:
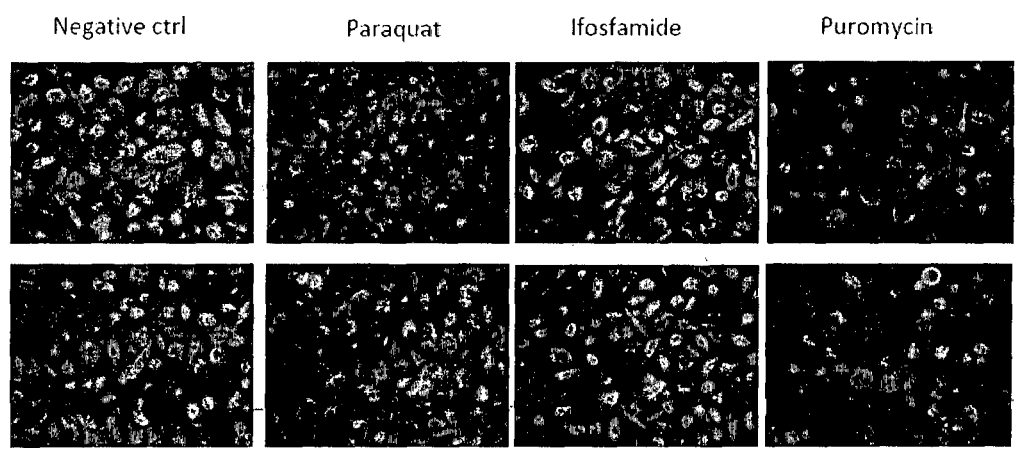
FIG. 13. Micrographs of HPTC that were left untreated (negative) control, or that were exposed to paraquat, ifosfamide or puryomycin at concentrations of 1000 µg/ml (upper row) or 500 µg/ml (lower row). Green: alpha-tubulin, blue: cell nuclei.

HPTC were cultured and treated as described in Examples 2 and 3, and left untreated or treated with the compounds as indicated in FIGS. 10-13. Cells were stained for F-actin (red; FIGS. 10 and 11) and tubulin (green; FIGS. 12 and 13). Cell nuclei were stained with DAPI (blue).

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

As used in this specification and the appended claims, the singular forms "a", "an" and "the" include plural reference unless the context clearly dictates otherwise. As used in this specification and the appended claims, the terms "comprise", "comprising", "comprises" and other forms of these terms are intended in the non-limiting inclusive sense, that is, to include particular recited elements or components without excluding any other element or component. As used in this specification and the appended claims, all ranges or lists as given are intended to convey any intermediate value or range or any sublist contained therein. Unless defined otherwise all technical and scientific terms used herein have the same meaning as commonly understood to one of ordinary skill in the art to which this invention belongs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

REFERENCES

1. E. M. Levy, C. M. Viscoli and R. I. Horwitz, *JAMA*, 1996, 275, 1489-1494.
2. D. Choudhury and Z. Ahmed, *Nat Clin Pract Nephrol*, 2006, 2, 80-91.
3. X. Guo and C. Nzerue, *Cleve Clin J Med*, 2002, 69, 289-290, 293-284, 296-287 passim.
4. K. Nash, A. Hafeez and S. Hou, *Am J Kidney Dis*, 2002, 39, 930-936.
5. B. S. Moffett and S. L. Goldstein, *Clin J Am Soc Nephrol*, 2011, 6, 856-863.
6. C. C. Szeto and K. M. Chow, *Ren Fail*, 2005, 27, 329-333.
7. M. A. Perazella, *Hosp Pract (Minneap)*, 2001, 36, 43-46, 55-46.
8. W. S. Redfern, L. Ewart, T. G. Hammond, R. Bialecki, L. Kinter, S. Lindgren, C. E. Pollard, R. Roberts, M. G. Rolf and J. P. Valentin, *The Toxicologist*, 2010, 114, 231.
9. H. Izzedine, M. Harris and M. A. Perazella, *Nat Rev Nephrol*, 2009, 5, 563-573.
10. P. P. Kapitsinou and N. Ansari, *J Med Case Rep*, 2008, 2, 94.
11. W. Pfaller and G. Gstraunthaler, *Environ Health Perspect*, 1998, 106 Suppl 2, 559-569.
12. P. Prieto, *Altern Lab Anim*, 2002, 30 Suppl 2, 101-106.
13. Y. Wu, D. Connors, L. Barber, S. Jayachandra, U. M. Hanumegowda and S. P. Adams, *Toxicol In vitro*, 2009, 23, 1170-1178.
14. Y. Li, Y. Zheng, K. Zhang, J. Y. Ying and D. Zink, *Nanotoxicology*, 2012, 6, 121-133
15. P. H. Bach, D. K. Obatomi and S. Brant, *In vitro methods for nephrotoxicity screening and risk assessment*, Academic Press Ltd, San Diego, 1997.
16. M. Bens and A. Vandewalle, *Pflugers Arch*, 2008, 457, 1-15.
17. S. E. Jenkinson, G. W. Chung, E. van Loon, N. S. Bakar, A. M. Dalzell and C. D. Brown, *Pflugers Arch*, 2012, 464, 601-611.
18. Z. Lin and Y. Will, *Toxicol Sci*, 2012, 126, 114-127.
19. T. Duff, S. Carter, G. Feldman, G. McEwan, W. Pfaller, P. Rhodes, M. Ryan and G. Hawksworth, *Altern Lab Anim*, 2002, 30 Suppl 2, 53-59.
20. W. Li, D. F. Choy, M. S. Lam, T. Morgan, M. E. Sullivan and J. M. Post, *Toxicol In vitro*, 2003, 17, 107-113.
21. W. Li, M. Lam, D. Choy, A. Birkeland, M. E. Sullivan and J. M. Post, *Toxicol In vitro*, 2006, 20, 669-676.
22. Limonciel, L. Aschauer, A. Wilmes, S. Prajczer, M. O. Leonard, W. Pfaller and P. Jennings, *Toxicol In vitro*, 2011, 25, 1855-1862.
23. I. Astashkina, B. K. Mann, G. D. Prestwich and D. W. Grainger, *Biomaterials*, 2012, 33, 4712-4721.
24. I. Astashkina, B. K. Mann, G. D. Prestwich and D. W. Grainger, *Biomaterials*, 2012, 33, 4700-4711.
25. C. Beeson, G. C. Beeson and R. G. Schnellmann, *Anal Biochem*, 2010, 404, 75-81
26. K. Narayanan, K. M. Schumacher, F. Tasnim, K. Kandasamy, A. Schumacher, M. Ni, S. Gao, B. Gopalan, D. Zink and J. Y. Ying, *Kidney Int*, 2013, 83, 593-603.

What is claimed is:
1. An in vitro method of screening for renal proximal tubular toxicity of a compound, the method comprising:
 contacting a test compound for which renal proximal tubular cell toxicity is unknown with a test population of renal proximal tubular cells grown attached to a support;
 measuring one or both of the following features of the renal proximal tubular cells in the test population: cell area, and area of nucleus: area of whole cell ratio;
 comparing the one or more features of the test population with the corresponding one or more features of a control population that has not been contacted with the test compound; and
 identifying the test compound as toxic for renal proximal tubular cells based on one or both of a decrease in cell area, and an increase in area of nucleus: area of whole cell ratio of the test population relative to the control population.
2. The method of claim 1, further comprising:
 determining cell numbers of the renal proximal tubular cells in the test population; and
 comparing cell count of the test population with cell count of a control population that has not been contacted with the test compound;
 wherein the identifying of the test compound as toxic for renal proximal tubular cells is further based on a decrease in cell numbers of the test population relative to the control population.
3. The method of claim 1, further comprising:
 examining arrangement of F-actin; and
 comparing the arrangement of F-actin of the test population with arrangement of F-actin of a control population that has not been contacted with the test compound;
 wherein the identifying of the test compound as toxic for renal proximal tubular cells is further based on a change in the arrangement of F-actin of the test population relative to the control population.

4. The method of claim 1, further comprising:
examining cell roundness; and
comparing the cell roundness of the test population with cell roundness of a control population that has not been contacted with the test compound;
wherein the identifying of the test compound as toxic for renal proximal tubular cells is further based on an increase in rounding of the proximal tubular cells of the test population relative to the control population.

5. The method of claim 1, further comprising prior to said examining and/or said determining, labeling the test population with a detectable label.

6. The method of claim 5, further comprising labeling the control population with the detectable label.

7. The method of claim 5, wherein the detectable label is a fluorescent label, or a coloured label.

8. The method of claim 5, wherein the detectable label is a nuclear label, a whole cell label, a cytoplasmic label, a label for cytoskeletal proteins or a cell surface label.

9. The method of claim 1, wherein the renal proximal tubular cells are derived from somatic cells or from stem cells.

10. The method of claim 9, wherein the renal proximal tubular cells are derived from somatic cells and are primary cells or are cells from a stable cell line.

11. The method of claim 10, wherein the renal proximal tubular cells are human primary renal proximal tubular cells, HK-2 cells, or LLC-PK1 cells.

12. The method of claim 9, wherein the renal proximal tubular cells are derived from stem cells and are differentiated from embryonic stem cells, mesenchymal stem cells, or induced pluriopotent stem cells.

13. The method of claim 1, wherein the renal proximal tubular cells are human renal proximal tubular cells.

14. The method of claim 1, wherein the renal proximal tubular cells are non-human renal proximal tubular cells.

15. The method of claim 1, wherein said contacting is performed over a period of time of about 8 hours or longer.

16. The method of claim 1, wherein said contacting is repeated one or more times in a period of from about 3 to about 14 days.

17. The method of claim 1, wherein said contacting comprises adding the test compound to the test population of renal proximal tubular cells at a concentration of about 0.001 to about 1000 μg/ml.

18. The method of claim 1, wherein the measuring comprises use of automated image analysis techniques.

19. The method of claim 1, further comprising:
examining arrangement of tubulin; and
comparing the arrangement of tubulin of the test population with arrangement of tubulin of a control population that has not been contacted with the test compound;
wherein the identifying of the test compound as toxic for renal proximal tubular cells is further based on a change in the arrangement of tubulin of the test population relative to the control population.

* * * * *